United States Patent [19]

Minter

[11] 4,452,065

[45] Jun. 5, 1984

[54] ROLLING CONTACT FATIGUE TEST ASSEMBLY

[75] Inventor: Marvin J. Minter, Ann Arbor, Mich.

[73] Assignee: Federal-Mogul Corporation, Detroit, Mich.

[21] Appl. No.: 297,489

[22] Filed: Aug. 28, 1981

[51] Int. Cl.³ .............................................. G01N 3/56
[52] U.S. Cl. .......................................... 73/7; 73/808
[58] Field of Search ................... 73/7, 10, 808, 810, 73/813, 824, 825, 64

[56] References Cited

U.S. PATENT DOCUMENTS

| 829,658 | 8/1906 | Leavitt | 308/189 A |
| 1,491,050 | 4/1924 | Lutz | 73/7 |

*Primary Examiner*—Jerry W. Myracle

[57] ABSTRACT

An assembly for testing the rolling contact fatigue of a test material including a collet for mounting the test material, spherical bearings for rolling contact with the test material, and a support structure for supporting the mounting collet and the spherical bearings for relative rotation therebetween. The assembly is characterized by the support structure including a pair of adjustable race members, each having an inclined or frustoconical surface in rolling contact with the spherical bearings for applying an adjustable predetermined force against the spherical bearings to force the bearings into rolling contact with the test material. A method of testing the rolling contact fatigue of the test material is also disclosed and includes the steps of disposing at least one of the spherical bearings in engagement with the test material and effecting relative rotation between the test material and the bearings, and characterized by adjustably wedging the spherical bearings against the test material to force the bearings into rolling contact with the test material.

20 Claims, 4 Drawing Figures

ROLLING CONTACT FATIGUE TEST ASSEMBLY

BACKGROUND OF THE INVENTION

1. Field of the Invention

The instant invention relates to an assembly for testing the rolling contact fatigue of a test material. The test material is of the type for manufacturing bearings or other parts subject to rolling contact with adjoining parts. In order to determine which of several materials is best suited for a particular use as, for example, a roller bearing in a specific assembly, a sample test material is subjected to rolling contact at a known pressure or force within a test instrument. The rolling contact fatigue life is determined from the initiation of the test to the time the test material fails, i.e., until the time the test instrument indicates that the test material has succumbed to fatigue. Several materials may be tested and the fatigue lives compared to determine which material is best suited for a particular use.

2. Description of the Prior Art

Full scale bearing tests constitute the ultimate proof of a bearing material, but these tests are expensive and time-consuming. A more effective and expedient way to study a large number of bearing materials is to use a bench tester for subjecting a test material of simple geometry to rolling contact fatigue. A primary goal in bench testing for rolling contact fatigue is to obtain data which is consistent and reliable. A second goal is to limit the complexity of the test instrument. Finally, it is crucial that the test material fail under the test conditions before the test instrument succumbs to the rolling contact fatigue.

The prior art rolling contact fatigue bench test instruments have been limited in their ability to fully and efficiently meet the above-mentioned goals. Prior art instruments sometimes produce results which are inconsistent between runs of several samples. The design of the test instrument is also quite complex. Often the instrument fails before the test material, resulting in vibrations which are falsely indicative of fatigue in the test material.

The instant invention provides a test instrument for obtaining more consistent data. It is simple in concept and design, and it includes means for ensuring that the test material fails in rolling contact fatigue before the test instrument.

SUMMARY OF THE INVENTION

The instant invention provides a test instrument for measuring the ability of a test material to withstand rolling contact fatigue. The test instrument includes a mounting collet for mounting the test material, a set of bearing elements for exerting rolling contact on the test material, and a support structure for supporting the mounting collet and the bearing elements for relative rotation between the mounting collet and the bearing elements. The assembly is characterized by the support structure including an adjustable wedge in rolling contact with the bearing elements for applying a predetermined but variable force against the bearing elements to urge the bearing elements into rolling contact with the test material.

Additionally, the instant invention provides a method of measuring the ability of a test material to withstand rolling contact fatigue. The method includes the steps of disposing a set of bearing elements in engagement with the test material and effecting relative rotation between the test material and the bearing elements. The method is characterized by wedging the bearing elements against the test material to urge the bearing elements into rolling contact with the test material under an accurately controlled load.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF PREFERRED EMBODIMENTS

Figure 1:
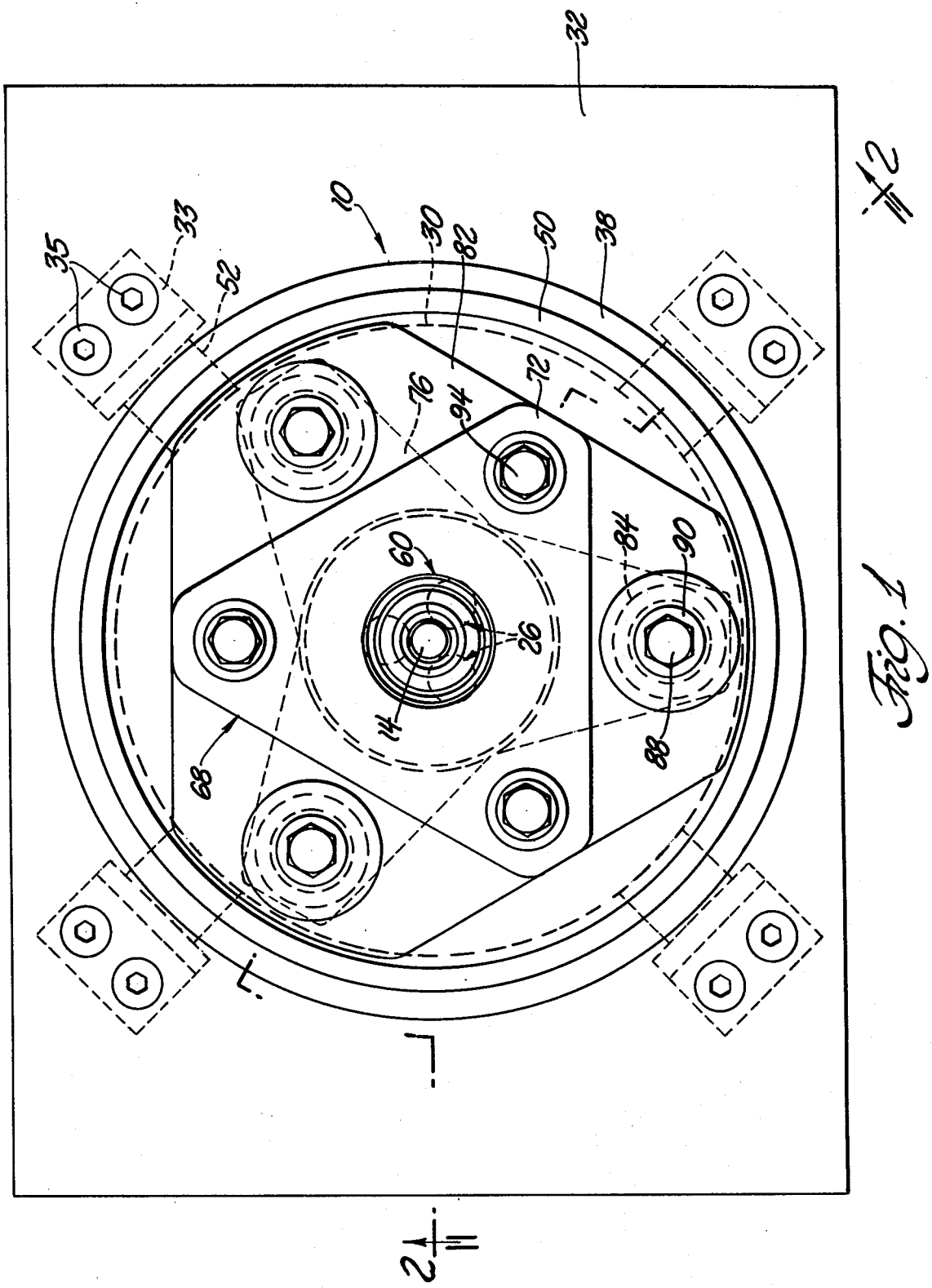
FIG. 1 is a top plan view of a preferred embodiment of the instant invention.

Two preferred embodiments of a test instrument for measuring the ability of a test material to withstand rolling contact fatigue constructed in accordance with the instant invention are generally shown at 10 in FIGS. 1 through 4. The two embodiments have common or like components which have like reference numerals and which are described first with the uncommon or unlike components described thereafter.

By way of introduction, the test instrument 10 is adopted to subject a test specimen 14 to rolling contact fatigue. This is accomplished by urging a set of spherical balls 26 against the test specimen 14 while the test specimen 14 is being rotated. The balls 26 are urged against the test specimen 14 by the wedging action produced by a special fixture generally shown at 68. The fixture 68 includes a pair of opposed race members 62 and 64 with wedge surfaces 66 and are urged axially toward one another under a controlled load. This load urges the wedge surfaces 66 against the balls 26 which urges the balls 26 radially into engagement with the test specimen 14.

Specifically, both assemblies 10 include mounting means, generally indicated at 12, for mounting the test specimen of material 14. The test specimen 14 is in the form of a rod having a length of approximately 3 inches and a diameter of $\frac{3}{8}$ inches. The mounting means 12 comprises an adjustable collet assembly including a first collar member 16 fixedly mounted on the drive shaft 18 of a direct drive motor 19 which is supported in a housing 20. The first collar member 16 includes an externally threaded upper portion and a tapered inner bore. A second segmented collar member 22 is located within the tapered bore of the first collar member 16 and includes an inner bore for receiving the test specimen. A lock nut 24 having an internally threaded cup-shaped portion is threaded onto the first collar member 16. The lock nut 24 forces the second collar member 22 into the tapered bore of the first collar member 16 to clamp or grip the test specimen. Thus, the test specimen 14 is operatively connected to the drive shaft 18 for rotation by the direct drive motor 19.

The instant invention further includes a set of bearing elements, generally indicated at 26, for subjecting the test specimen to rolling contact. The bearing elements 26 comprise a plurality of spherical balls 26. Three spherical balls 26 are disposed symmetrically, that is 120° apart, about the test specimen 14. The exact number of spherical balls 26 is not critical, however, tests have shown that the use of three spherical balls 26 provides stability under test conditions.

Frequently, standard spherical balls have relatively smooth surfaces and cause the time to failure during testing to be beyond acceptable test limits. Consequently, the balls are uniformly roughened to increase the stresses on the test specimen. The balls may be roughened by various techniques such as by sand or grit blasting.

While standard balls have surface finishes typically under 0.5 microinches AA (arithmetic average), good test results have been obtained with balls having a surface finish of at least 3.5 microinches AA. The test rod has surface finish in the range of 2 to 3 microinches AA.

Support means, generally indicated at 28, supports the mounting means 12 and the bearing means 26 for relative rotation therebetween. The support means 28 also includes the motor housing 20 which supports the motor 19 for rotating the mounting means 12.

The support means 28 is secured to a table or platform 32 by brackets 33 and screws 34 and 35. The table 32 has an opening 36 therethrough, assembly 10 being disposed through the opening 36. A basin member 38 is supported by the mounting plate 30 and an annular seal 39 is disposed therebetween. The basin 38 includes a central bore 40. A well wall 42 surrounds the mounting means 12 and has a top portion defining a platform having a gasket 44 thereabout. To dampen vibration the well wall 42 further defines a reservoir for a liquid lubricant 41, such as oil or other lubricants.

An annular member 43, U-shaped in cross section, is disposed at the bottom of the reservoir and between the plate 30 and the drive shaft 18. Two annular resilient members 45 and 47 are supported about the inner leg of the annular member 43 by a spring 49, thereby perfecting a seal about the drive shaft 18. The spring 49 also biases the annular member 43 into position at the bottom of the reservoir.

The well wall 42 further includes an outlet 46 allowing for the escape of excess lubricant from the reservoir within the well wall 42. The lubricant is collected in the basin 38 and flows through the opening 40 between the basin 38 and the well wall 42. The mounting plate 30 includes a threaded port 48 which is adapted to be connected to a fluid recirculation means which would recirculate the fluid back to the assembly for reuse or disposal or to a reservoir.

The support means 28 further includes a splash wall 50 surrounding the assembly and extending upwardly from the basin 38 to an open top. An annular seal 51 is disposed between the basin 38 and the splash wall 50. During test runs, lubricant is dripped onto the rotating test rod 14. The splash wall 50 collects lubricant being thrown off by the test material 14, the lubricant being collected in the basin 38 for use as described above.

The support means 28 further includes vibration dampening means 52 for connecting the support means 28 to the support table 32 and dampening vibrations therebetween. The vibration dampening means 52 consists of rubber members or blocks 52 mounted on the bolts 34 between the support brackets 33 and the mounting plate 30. As previously stated, the mounting brackets 33 are connected to the support table 32 by the screws 35. Thusly, any external vibrations are absorbed by the rubber members 52 thereby isolating the assembly 10 from external vibrations.

As stated above, the fixture produces a wedging action on the balls 26 that urges them into contact with the test specimen 14. The fixture is capable of applying a predetermined and adjustable force against the balls 26 to control the force exerted on the test specimen 14.

The fixture includes wedge means 60 comprising first and second race members 62 and 64. Each race member 62 and 64 has an inclined surface 66 in rolling engagement with the balls 26. The inclined surfaces 66 each define a frustoconical inner race surface in each of the race members 62 and 64. The frustoconical inner surfaces 66 of the race members are opposed and in wedging engagement with the balls 26 so that the wedging force applied thereby urges the race members 62 and 64 together against the bearings 26.

The assembly could only include a single wedge member having an inclined surface in rolling engagement with the bearing member 26. The single wedge member would be actuated to force the bearing member 26 inwardly against the test material 14 while axial movement of the bearing member 26 is restrained by a second flat race.

The spherical bearing members 26 are spaced annularly about the race members 62 and 64 by a cage member 80. The cage member 80 is preferably made of bronze. The cage member 80 includes openings spaced annularly thereabout in which the spherical bearing members 26 are caged. The openings also allow the bearing members 26 to be exposed to the test rod 14 and further provide sufficient space for the slight inward and outward movement of the bearing members 26 in response to the wedging action of the race members 62 and 64.

The wedge means 60 further includes a force-applying means, generally indicated at 68 for forcing the inclined or wedging surfaces 66 of the race members 62 and 64 into wedging engagement with the bearing members 26. In other words, the force-applying means 68 applies a predetermined force to clamp together the race members 62 and 64 so as to force the bearing members 26 radially inwardly against the test rod 14 under test conditions.

The force-applying means 68 has an opening 70 therethrough surrounding the mounting means 12 and test rod 14 above the reservoir defined by the well wall 42 for allowing liquid, such as oil or other lubricants, to pass therethrough and into the reservoir for use as previously described.

Figure 2:
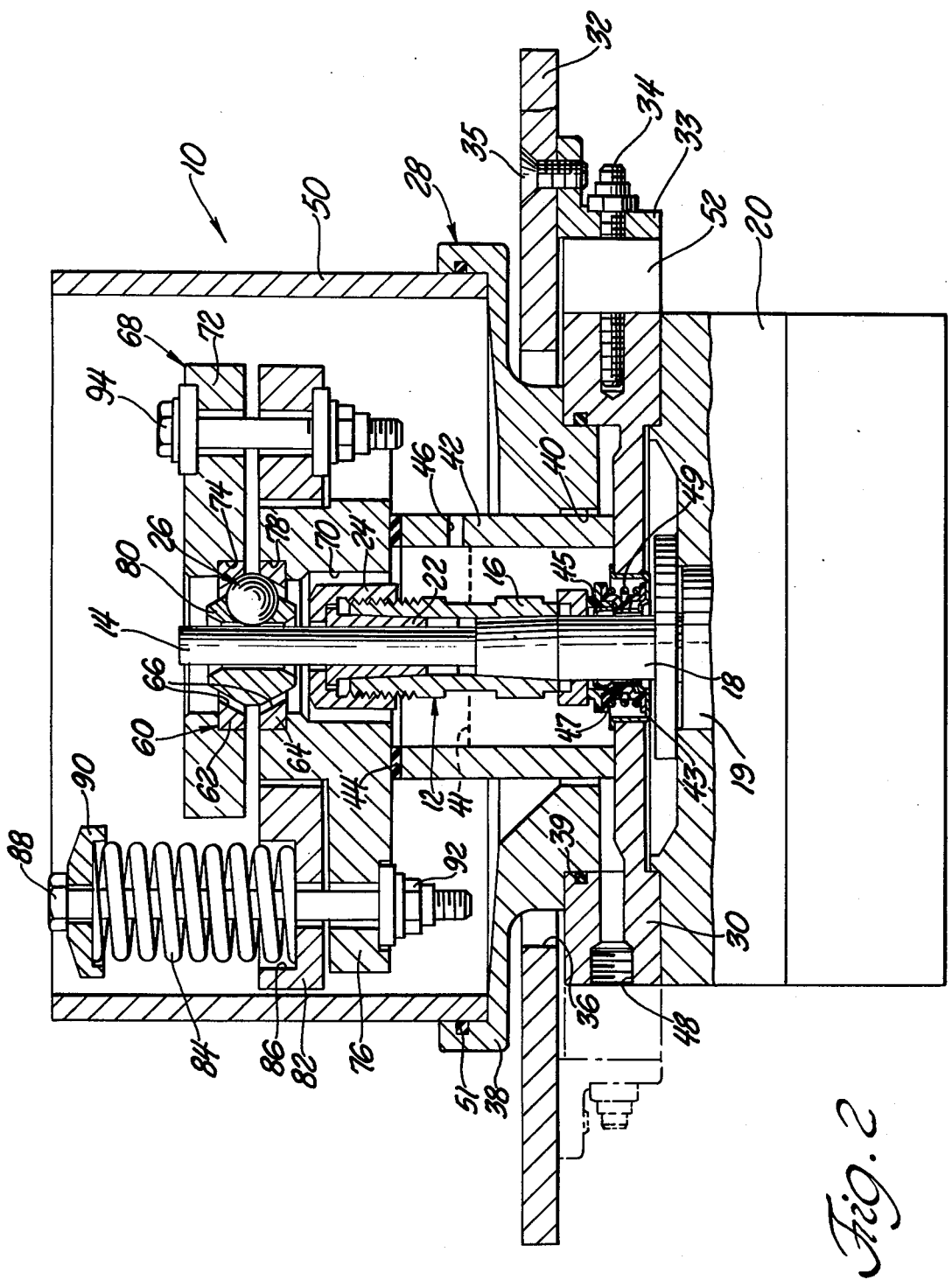
FIG. 2 is a cross-sectional view taken substantially along lines 2—2 of FIG. 1.

Referring only to the embodiment of FIGS. 1 and 2, the force-applying means 68 includes a first plate member 72 having an annular recess 74 for supporting the first race member 62. The force-applying means 68 further includes a second plate member 76 having an annular recess 78 for supporting the second race member 64.

The second plate member 76 is removably supported on the gasket 44 on the platform defined by the well wall 42. In other words, the entire force-applying means 68, when not gripping or clamping the test rod 14, may be removed from within the splash wall 50, i.e., no bolts or other connecting means are necessary to secure the force-applying means 68 to the support means 28.

The force-applying means 68 further includes adjustable biasing means for urging the plates 72 and 76 together under a predetermined force. The biasing means includes a third plate member 82 disposed between the first and second plate members 72 and 76. A plurality of springs 84 are spaced about the plate members 72, 76 and 82. The springs are seated within cup-shaped depressions 86 in the third plate member 82. A bolt member 88 secures a retaining cup 90 to the other end of the spring 84. A calibration nut 92 secures the bolt to the second plate member 76 for adjustably presetting the force of the spring 84 to bias the third plate member 82 toward the second plate member 76. In other words, the bolts 88 associated with each spring 84 extend through the second plate member 76 and through each spring 84 and the springs 84 react with the second plate member 76 to compress each spring 84 against the third plate member 82.

The biasing means further includes a second plurality of load-applying bolts 94 spaced about the first and third plate members 72 and 82 and extending therethrough for limiting the separation of the first and third plate members 72 and 82.

In operation, the bolts 88 and nuts 92 adjust the pressure or force applied by the springs 84 on the second and third plates 76 and 82. Since the third plate 82 is secured to the first plate 72 by bolts 94, the increased force applied by the springs 84 clamps the upper first race member 62 axially downwardly toward the bottom race member 64 thereby forcing the bearing members 26 radially inwardly against the test rod 14. In other words, the inward radial force of the bearing members 26 on the test rod 14 is controlled by the adjustable bolts 88 and 94.

The spring load is first preset by adjustment of the calibration nuts 92. The load is properly adjusted when a load applied by a calibrated dead weight causes separation of the third plate 82 from the second plate 76. Thusly, the load is preset once for a series of tests and need not be reset before each test, as would be the case if the first and second plate members 72 and 76 were directly connected.

During a test, the stress level of the test rod 14 is determined assuming no plastic deformation. From this data the approximate spring load is determined. Other factors that are considered are the oil used, the viscosity of the oil and the ambient temperature. The tests are generally run at room temperature. Once the test rod 14 is mounted within the mounting means 12 and the spring force is determined, the test is run until the test rod fails from rolling contact fatigue. The failure is detected by vibration level increase with a vibration transducer (not shown) which is connected to one of the bolts 94 or 88 or plates 72, 82 or 76.

Figure 3:
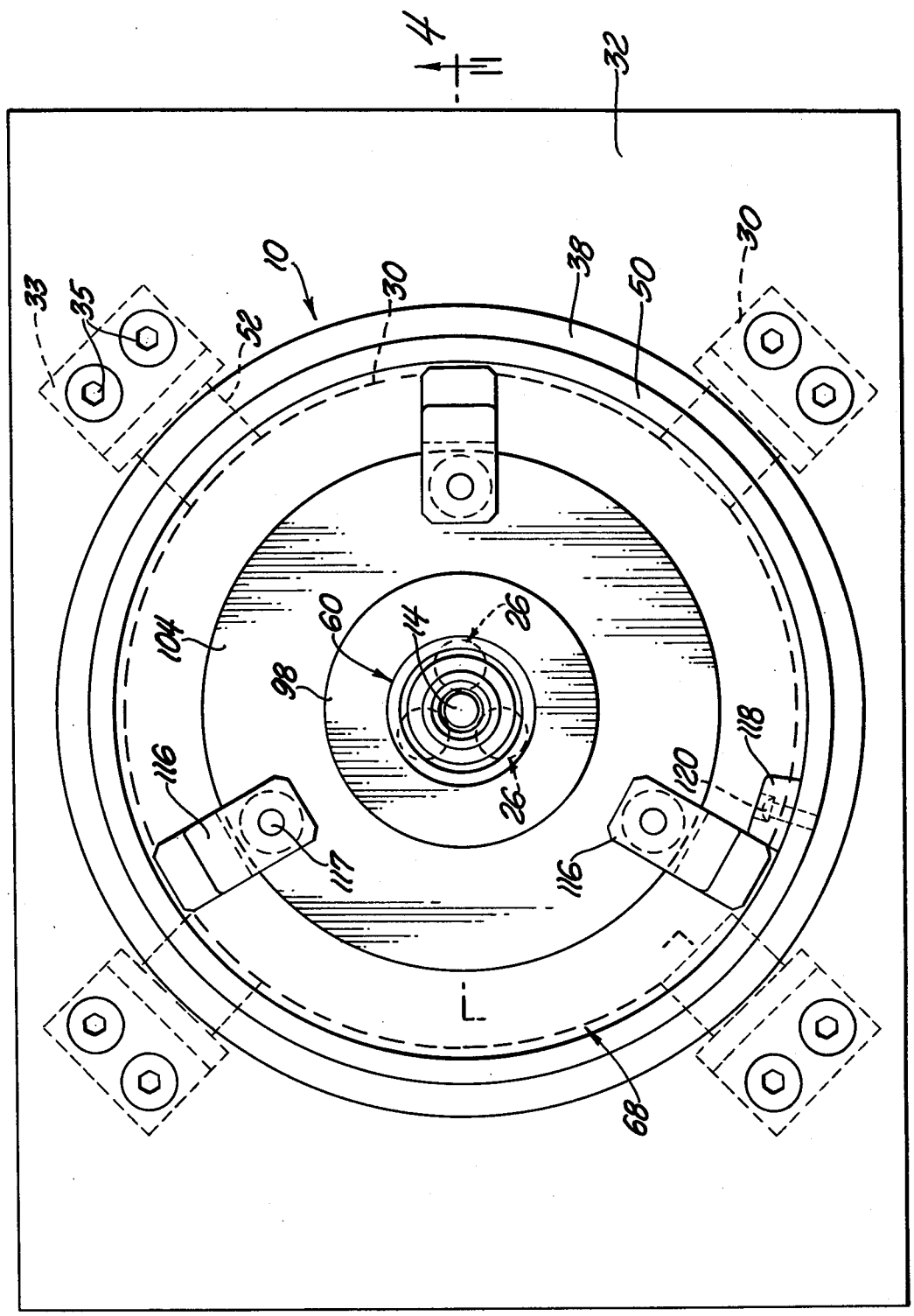
FIG. 3 is a top plan view of a second preferred embodiment of the instant invention.
Figure 4:
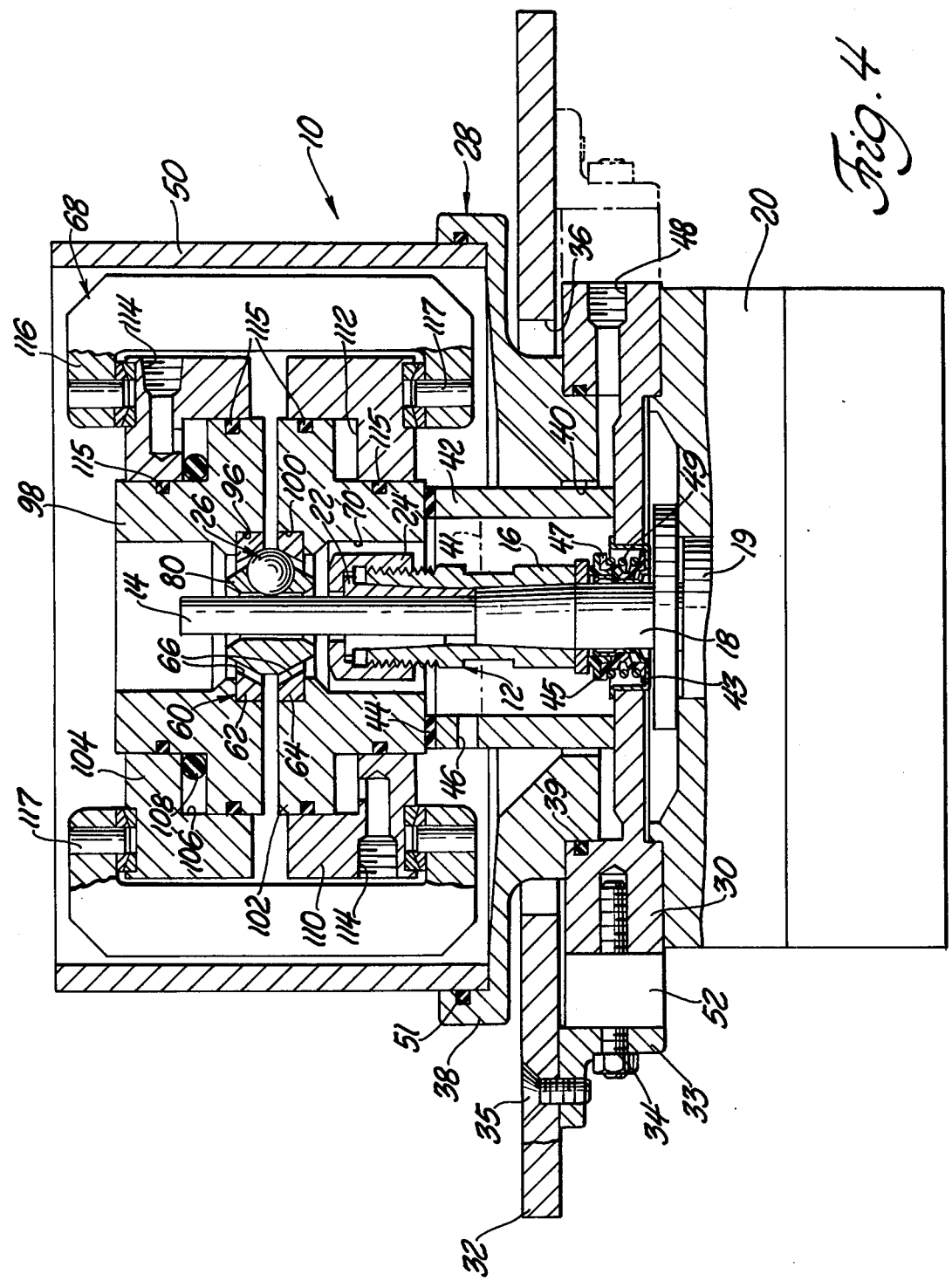
FIG. 4 is a cross-sectional view taken substantially along line 4—4 of FIG. 3.

Referring now only to the embodiment of FIGS. 3 and 4, the force-applying means 68 includes a first plate member defined by the upper piston member 98 and a second plate member defined by the lower piston member 102. The first race member 62 is supported within an annular groove 96 in upper piston member 98. The second race member 64 is supported in an annular groove 100 in bottom piston member 102. The upper piston member 98 is movably disposed in a first hydraulic cylinder 104 to define a first hydraulic chamber 106 therebetween. An O-ring 108 is disposed within the chamber 106 and prevents the chamber 106 from bottoming out, as will be described below. The bottom piston member 102 is movably disposed in a second hydraulic cylinder 110 to define a second hydraulic chamber 112. The first and second cylinders 104 and 110, respectively, each include hydraulic fluid inlets 114 to allow the ingress and egress of hydraulic fluid from the chambers 106 and 112. O-rings 115 are disposed between the cylinders 104 and 110 and the pistons 98 and 102 to perfect seals about the chambers 106 and 112, respectively. Thus, in the second embodiment the biasing means is hydraulic pressure for urging the race supporting plate members together.

The assembly further includes connecting means comprising a plurality of clamps 116 interconnecting the cylinders 104 and 110 for maintaining the cylinders 104 and 110 in fixed relationship to one another. The connecting means includes pins 117 securing the clamps 116 to the cylinders 104 and 110.

The bottom piston member 102 is removably supported upon the gasket 44 on the well wall 42. Thus, as described for the first embodiment, the entire force-applying means 68 can be removed between test runs and requires no additional fastening or connecting means to secure the force-applying means 68 on the support means 28.

The O-ring 108 defines a spacer means in the first hydraulic chamber 106 for limiting the closure thereof. Since the bottom piston member 102 supports the entire force-applying means 68 by resting upon the gasket 44 on the platform of the wall 42, the weight of the cylinders 104 and 110 would tend to bottom out and close the upper first chamber 106. The O-ring 108 limits the closure of the first hydraulic chamber 106 thereby maintaining a volume in the first chamber 106 when there is no hydraulic pressure within the chambers.

A rubber bumper or stop member 118 is connected to the splash wall 50 by a screw 120, the head of the screw 120 being recessed within the bumper 118. The bumper 118 abuts one of the clamps 116 thereby preventing rotation of the force-applying means 68. The bumper 118 is necessary since the force-applying means 68 is seated on the wall 42 without any connecting means securing the force-applying means 68 thereto. A similar bumper can be used to prevent rotation of the assembly shown in FIGS. 1 and 2.

In operation, the load on the spherical bearings 26 is determined by the hydraulic force exerted upon the pistons 98 and 102. The wedging of the bearings 26 between the races 62 and 64 is the same as the operation previously described in connection with the first embodiment.

The instant invention therefore provides a method of measuring the ability of a test material 14 to withstand rolling contact fatigue. The method includes the steps of disposing the bearing elements 26 in engagement with the test material 14 and effecting relative rotation between the test material 14 and the bearing elements 26. The method is characterized by adjustably wedging the bearing elements 26 against the test material 14 to force the bearing elements 26 into rolling contact with the test material 14.

The bearing elements 26 are adjustably wedged against the test material 14 by engaging the bearing elements 26 with at least one race member 62 having an inclined surface 66 in rolling engagement with the bearing elements 26. A force is applied to the race member 62 to force the inclined surface 66 thereof into wedging engagement with the bearing elements 26.

The invention has been described in an illustrative manner, and it is to be understood that the terminology which has been used are intended to be in the nature of words of description rather than of limitation.

Obviously, many modifications and variations of the present invention are possible in light of the above teachings. It is, therefore, to be understood that within the scope of the appended claims wherein reference numerals are not to be in any way limiting, the invention may be practiced otherwise than as specifically described.

The embodiments of the invention in which an exclusive property or privilege is claimed are defined as follows:

1. An assembly for measuring the ability of a cylindrical test material specimen (14) to withstand rolling contact fatigue, said assembly comprising mounting means (12) for mounting the cylindrical test material specimen (14), bearing means (26) for rolling contact with the cylindrical test material specimen (14), support means (28) for supporting said mounting means (12) and said bearing means (26) for relative rotation between said mounting means (12) and said bearing means (26), said support means (28) including wedge means (60) in rolling contact with said bearing means (26) for applying an adjustable predetermined and variable force against said bearing means (26) to urge said bearing means (26) into rolling contact with the cylindrical test material specimen (14), said wedge means (60) including at least one wedge member (62) having a first annular race member (62) disposed about the cylindrical test material specimen (14), said first annular race member (62) including an inclined surface (66) defining a substantially frustoconical inner race surface (66) on said race member (62) and being in rolling engagement with said bearing means (26), said wedge means (60) further including a force-applying means (68) for forcing said inclined surface (66) of said wedge member (62) into wedging engagement with said bearing means (26) to thereby apply a determinable preload between said bearing means (26) and the cylindrical test material specimen (14), and said mounting means (12) including an adjustable collet (22) rotatably supported by said support means (28) for clamping engagement with the cylindrical test material specimen (14).

2. An assembly as set forth in claim 1 wherein said support means (28) further includes a platform (44) positioned about said collet (22), said force-applying means (68) being supported on said platform (44).

3. An assembly as set forth in claim 2 including a well wall (42) surrounding said collar (22) and having a top defining said platform (44), said well wall (42) defining a reservoir for liquid and including an outlet (46), said force-applying means (68) having an opening (70) therethrough surrounding said collet (22) and test material (14) and disposed above said reservoir for allowing liquid to pass therethrough and into said reservoir.

4. An assembly as set forth in claim 3 wherein said support means (28) includes a splash wall (50) extending upwardly to an open top and surrounding said force-applying means (68).

5. An assembly as set forth in claim 1 wherein said wedge means (26) includes a second annular race member (64) having a substantially frustoconical inner race surface (66) engaging said bearing (26) in opposed wedging engagement to said first race member (62) so that said force-applying means (68) urges said race members (62, 64) together against said bearing (26).

6. An assembly as set forth in claim 5 wherein said force-applying means (68) includes a first plate member (72, 98) supporting said first race member (62) and a second plate member (72, 102) supporting said second race member (64), and adjustable biasing means for urging said plates (72, 76, 98, 102) together under said predetermined force.

7. An assembly as set forth in claim 6 wherein said second plate member (76, 102) is removably supported on said platform (44).

8. An assembly as set forth in claim 6 wherein said bearing means includes a plurality of spherical bearings (26) and a cage member (80) spacing said bearings (26) annularly about the race members (62, 64).

9. An assembly as set forth in claim 8 including drive means (20) supported by said support means (28) for rotating said collet (22).

10. An assembly as set forth in claim 8 wherein said support means (28) includes vibration dampening means (52) for connecting said support means (28) to a structure (32) and dampening vibrations therebetween.

11. An assembly as set forth in claim 8 wherein said biasing means includes at least one spring (84) urging said plate members (72, 76) together.

12. An assembly as set forth in claim 11 wherein said biasing means includes a third plate member (82) disposed between said first and second plate members (76), a plurality of said springs (84) being spaced about said plate members (72, 76, 82), bolt means (88) associated with each spring (84) and extending through said second plate member (76) to the top of each spring (84) for reacting with said second plate member (76) to compress each spring (84) against said third plate member (82), a second plurality of bolts (94) spaced about said plate members (72, 76, 82) and extending through said first and third plate members (72, 82) for limiting the separation of said first and third plate members (72, 82).

13. An assembly as set forth in claim 8 wherein said biasing means includes hydraulic means urging said plate members (98, 102) together.

14. An assembly as set forth in claim 13 wherein said hydraulic means includes a first hydraulic cylinder (104) and a second hydraulic cylinder (110), said first plate member (98) defining an upper piston member (98) movably disposed in said first hydraulic cylinder (104) to define a first hydraulic chamber (106), said second plate member (102) defining a lower piston member (102) movably disposed in said second hydraulic cylinder (110) to define a second hydraulic chamber (112).

15. An assembly as set forth in claim 14 including connecting means (116, 117) interconnecting said cylinders (104, 110) and maintaining said cylinders (104, 110) in fixed relationship to one another.

16. An assembly as set forth in claim 15 wherein said support means (28) includes a platform (44) positioned about said collet (22), and said lower piston member (102) removably rests upon said platform (44).

17. An assembly as set forth in claim 16 including spacer means (108) in said first hydraulic chamber (106) for limiting the closure of said first hydraulic chamber (106).

18. An assembly as set forth in claim 1 wherein said bearing means (26) includes at least one spherical bearing (26).

19. An assembly as set forth in claim 18 wherein said spherical bearing (26) has a roughened surface.

20. A method of measuring the ability of a cylindrical test material specimen (14) to withstand rolling contact fatigue including the steps of, disposing a plurality of spherical bearing elements (26) about the circumference of the cylindrical test material specimen and in engagement therewith in line contact lying in a plane transverse to the axis thereof, adjustably wedging the bearing elements (26) against the cylindrical test material specimen (14) to force the bearing elements (26) into rolling contact therewith by engaging the bearing elements (26) with a wedge member (62) having an inclined surface (66) in rolling engagement with the bearing elements (26), applying a predetermined force to the wedge member (62) to force the inclined surface (66) thereof into wedging engagement with the bearing elements (26), thereby causing said bearing elements to engage said cylindrical test material specimen at a predetermined load, and effecting relative rotation between the cylindrical test material specimen (14) and the bearing elements (26) at said predetermined load for a period of time sufficient to determine the rolling contact fatigue strength of said cylindrical test material specimen.

* * * * *

UNITED STATES PATENT AND TRADEMARK OFFICE
CERTIFICATE OF CORRECTION

PATENT NO. : 4,452,065
DATED : June 5, 1984
INVENTOR(S) : Marvin J. Minter

It is certified that error appears in the above-identified patent and that said Letters Patent is hereby corrected as shown below:

Col. 8, line 1 (Claim 6) "(72, 102)" should be --(76, 102)--

Signed and Sealed this

Thirtieth Day of April 1985

[SEAL]

Attest:

DONALD J. QUIGG

Attesting Officer    Acting Commissioner of Patents and Trademarks